United States Patent
Pedersen et al.

[11] Patent Number: 5,609,482
[45] Date of Patent: Mar. 11, 1997

[54] ORTHODONTIC BRACE

[76] Inventors: Erik H. Pedersen, Engskovvej 48, DK-8541 Skoedstrup; Kim L. Andersen, Graven 14, 2, DK-8000 Aarhus C, both of Denmark

[21] Appl. No.: 325,238
[22] PCT Filed: Apr. 27, 1993
[86] PCT No.: PCT/DK93/00139
 § 371 Date: Dec. 15, 1994
 § 102(e) Date: Dec. 15, 1994
[87] PCT Pub. No.: WO93/21854
 PCT Pub. Date: Nov. 11, 1993

[30] Foreign Application Priority Data

May 1, 1992 [DK] Denmark ............... 0566/92

[51] Int. Cl.$^6$ ............................................ A61C 7/00
[52] U.S. Cl. ............................................ 433/18; 433/21
[58] Field of Search ............................ 433/18, 19, 21

[56] References Cited

U.S. PATENT DOCUMENTS

| | | | |
|---|---|---|---|
| 3,798,773 | 3/1974 | Northcutt | 433/19 |
| 4,311,463 | 1/1982 | Glattly | 433/18 |
| 4,551,095 | 11/1985 | Mason | 433/19 |
| 4,849,032 | 7/1989 | Kawaguchi | . |
| 5,011,404 | 4/1991 | Losi | 433/21 X |
| 5,044,947 | 9/1991 | Sachdeva et al. | 433/20 |
| 5,102,333 | 4/1992 | Suzuki et al. | 433/24 |
| 5,378,147 | 1/1995 | Mihailowitsch | 433/18 X |

*Primary Examiner*—Robert P. Swiatek
*Assistant Examiner*—Elizabeth Shaw
*Attorney, Agent, or Firm*—Watson Cole Stevens Davis, P.L.L.C.

[57] ABSTRACT

An orthodontic brace which is easy to use and which will optimize the relation between moment and force includes a guide mechanism that includes an upper bending stable mounting bar, two lower mounting bars, and substantially rectilinear wires connected between the upper mounting bar and each of the lower mounting bars. The lower mounting bars are fastened to an arch wire or a bracket on the teeth desired to be moved by fastening locks. As the springs of the orthodontic brace are made up of the wires, which are made from a superelastic material, and which are fixed in the bars, a desired moving, in relation to another tooth segment, may be obtained in form of a translation, which possibly is combined with a rotation of a tooth segment. The desired movement depends on the form of the guide mechanism. The applied force will substantially be constant, and due to the torsion stable guide mechanism, which with torsion stability is connected with a tooth to be moved, a self-adjusting contribution of moment is obtained. Consequently, an unintended rotation is obviated during movement.

10 Claims, 7 Drawing Sheets

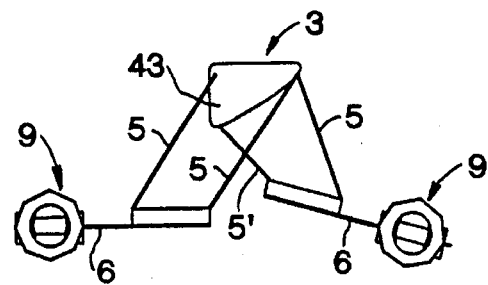
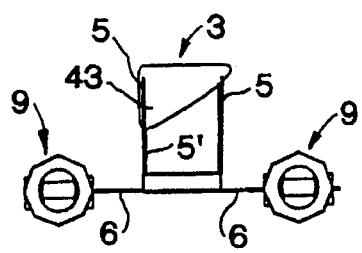
Fig. 12        Fig. 13
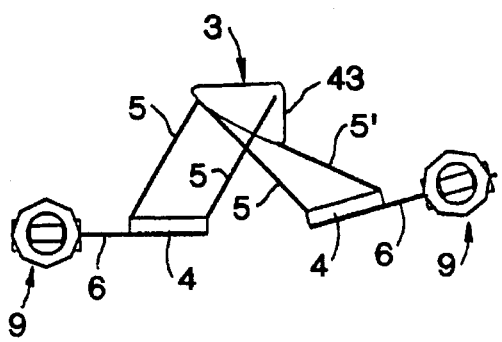
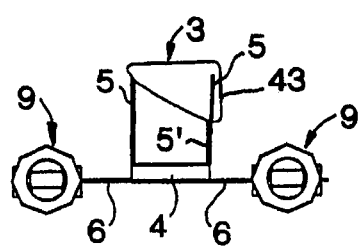
Fig. 14        Fig. 15
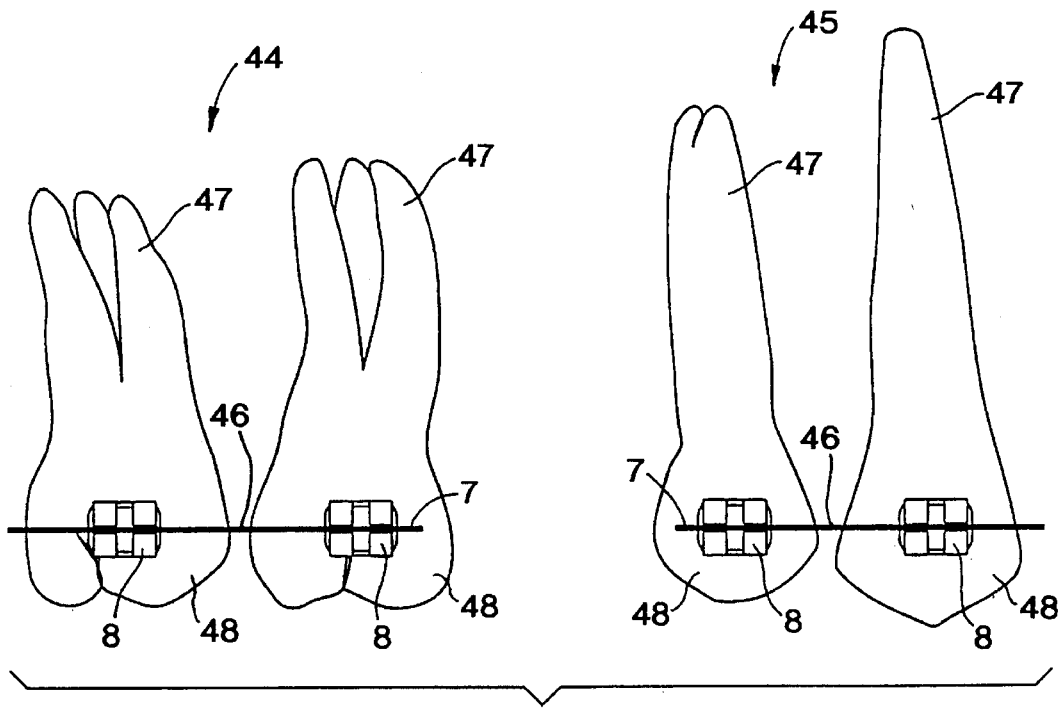
Fig. 16

ORTHODONTIC BRACE

BACKGROUND OF THE INVENTION

1. Field of the Invention

The present invention relates to an orthodontic brace of the type that includes spring formed of a superelastic material for establishing movement of the teeth desired to be moved, and fastening means which are intended for fastening the spring means to force-transmitting means which are connected with the teeth for transmitting the actuation force of the spring means to the teeth desired to be moved.

2. The Prior Art

For a correction of misaligned teeth small locks are placed on the teeth, these locks are so-called brackets, in which it is possible to mount different types of wires, depending on the type of tooth movement desired to be carried out.

In the majority of all cases orthodontics is carried out by means of continuous arches along which the tooth movements are carried out. This technique, which is called the straight-wire-technique, is connected with drawbacks as friction arises between the locks and the wires, and as it is difficult to carry out a parallel translation along the arch. Furthermore, it is only possible to carry out tooth movements in the direction of the arch.

In order to overcome the drawbacks of the straight-wire-technique, a so-called segmented technique has been developed in which specially shaped braces are applied between groups of teeth, which braces supply forces and momenta resulting in the tooth movements. Using this technique the correction of the misaligned teeth may be controlled in a more precise way.

However, this requires a thorough knowledge of the relations between the geometry of the teeth, bone support, and the mechanical properties of the braces. It is especially important to have a precise knowledge of how forces and momenta are released from these braces in order to obtain a desired tooth movement. Though the arches remedy some of the drawbacks of the straight-wire-technique, they are complicated to use as great degree of manual adjusting and a large professional skill is required in order to correctly apply and use the known braces. Furthermore, the known braces will not make it possible in all situations to obtain desired relations between moment and force during tooth movement, which occurs after applying the known braces.

It is also difficult to relate the forces and momenta directly to the so-called centre of resistance for a tooth. The centre of resistance is defined as the point through which the effect from simple force will result in a translation. The centre of resistance will normally be positioned approximately in the centre of a root of a tooth, that is to say, in the jawbone approximately ⅓ from the tip of the root. As the teeth are affected via brackets which are positioned on the crowns of teeth, a simple force acting on a bracket will result in a combined translation and rotation of a tooth or a tooth segment which is affected. On the contrary, a pure translation of a tooth is obtained by applying a combined force and a moment on the brackets used. When the relation between the applied moment and the applied force vary, different tooth movements are obtained, which may be a pure translation, a combined translation and rotation, or a simple rotation around the centre of resistance.

A drawback of the known techniques is the need for optimizing the actuation on the teeth in order to obtain tooth movement relative to biomechanical properties. Thus, it is desired to keep the force actuation within limits in which an optimizing of the biomechanical system occurs, so that tooth movement takes place with a speed that is as optimal as possible. This relation should also be compared to the desire to minimize adjustments of the actuation means, as this normally requires a consultation.

Another important aspect is that a tooth movement with great actuation force will also cause much unpleasantness for the patient. Accordingly, through experience it has been found that an optimal force should be between approximately 50 cN and 250 cN. In order to obtain such a comparative, well-defined and constant force, it has been previously suggested, e.g., from U.S. Pat. No. 4,849,032, to use springs from a superelastic material, as a substantially constant force may be obtained over a comparatively long spring compression. That is to say, establishment of springs which do not follow Hookes' Law of linear elastic materials.

Though the use of the superelastic springs will highly comfort the patient and simultaneously give the possibility of less frequent consultations for checking the orthodontic brace, the use will not remedy the above-mentioned drawbacks with uncertain tooth movements.

It is the object of the present invention to remedy the above-mentioned drawbacks and to provide an orthodontic brace which also makes it possible to carry out orthodontic correction of misaligned teeth according to the two known fundamentals, that is to say, with the straight-wire-technique and the segmented technique, and which simultaneously will be very easy to use and wherein a precise and unique tooth movement is obtained. At the same time, it is the object that the orthodontic brace can be prefabricated, and that there will be no subsequent need for individual adjustment and adaption when using the orthodontic brace.

SUMMARY OF THE INVENTION

These objects are attained according to the present invention with an orthodontic brace of the above-mentioned type, characterized in that the orthodontic brace includes a guiding mechanism with a bending stable, upper mounting bar and two bending stable, lower mounting bars which extend substantially parallel to the upper mounting bar, and which by means of the fastening means is fastened for forced rotation together with the force-transmitting means, which may optionally be constituted of a bracket adhered to a tooth or an arch wire connected with several teeth via brackets, that the upper mounting bar is connected with each of the lower mounting bars by means of at least two substantially rectilinear and parallel wires, and that the spring means resiliently actuate the two lower mounting bars.

With such an orthodontic brace it will be possible to obtain a substantially constant actuation force, which may be optimized within the desired force level, irrespective of whether a straight-wire-technique is used in which the guide mechanism is connected with an arch wire, or a segmented technique in which the guide mechanism is connected with a bracket directly onto a tooth or a tooth segment. It will also be possible to use a straight-wire-technique in combination with a segmented technique on the tooth or the tooth segment, which is located adjacent an orthodontic brace, which is inserted instead of a portion of a traditional arch wire.

With an orthodontic brace according to the invention a self-adjusting contribution of moment is formed. Because of the structure of the guide mechanism with a joint connection between the upper mounting bar and each of the lower mounting bars, the orthodontic brace will not incur a moment on the teeth. Here it is a condition that the joint connection between the bars is constituted of wires having identical lengths for obtaining a translation.

First the spring means are tightened in such a way that a joining or separating force is obtained between the two lower mounting bars. This causes an initial translation of the tooth or teeth desired to be moved, and possibly give rise to a moment because of the forced rotation connection between a mounting bar and a force-transmitting means. Because of the forced rotation connection any tendency to mutual rotation will be conteracted by an opposite acting moment. At once when the tendency to mutual rotation disappears, and thus only a pure translational displacing of the tooth or teeth appears, the established moment will disappear too. Thus, the system does not give risk of moving the teeth in form of rotation, which may cause incorrect movement of the root or crown.

As the mounting bars are bending stable, or in any case have such a bending stability to transmit forces which are formed by activating the spring means, a tooth movement will always occur according to the mutual movement of the two lower mounting bars, which is determined by the length of the wires. As a self-adjusting moment is also obtained, the tooth movement will always be a translational movement with the mutual orientations of the teeth, which initially are established through the forced rotation connection between the mounting bars and the force-transmitting means, which are fastened to the tooth or the tooth segment desired to be moved.

According to the invention the orthodontic brace is very flexible as the force/moment combination, which is established by means of the brace, may very easily be controlled merely by changing the length of one of the wires for the lower mounting bar or both the lower mounting bars. This may easily be established when the upper mounting bar is made from moulded materials, preferably plastics. By forming a projecting portion on the upper and/or lower mounting bar and connecting the wire hereto, the length of the wire is changed, and hereby a joining or separating movement of the two mounting bars will not occur according to a straight line but through a swinging movement. Because of the forced rotation connection with the force-transmitting means on the tooth or teeth, this swinging movement will give rise to a force/moment combination. The relation between the moment and the force may rather easily be adjusted, and due to the use of a superelastic spring, it will be a constant relation, irrespective the degree of contraction or separation of teeth, which is established with the orthodontic brace. Thus, by segmented moving of a single tooth, a movement may be established in which both the moment and the force will be constant during the movement. Consequently, the tooth desired to be moved may be provided with a combined translation and rotation. Hereby, it will be possible to carry out a simultaneous translation and rotation of a tooth or a tooth segment.

The use of the orthodontic brace for actual orthodontic correction of misaligned teeth will be simple. The mounting of the orthodontic brace will also be simple with fastening means which will actually be put on like a clip by guiding the U-shape around the rod-shaped portion of the lower mounting bars and an arch wire or a rod-shaped portion, which are intended for engaging a single bracket by a segmented tooth movement.

The fastening means ensure that the orthodontic brace is torsion stable. It will be easy to adjust after being mounted. The pawl is merely displaced by turning the nut. Consequently, the rods or the wires, which are accommodated in the interior of the U, are fastened. Before complete tightening of the two nuts a tensioning of the spring means is carried out. After the nut is tightened the spring means will be secured in the tensioned state. This tensioning may easily and uncritically be carried out as a very precise adjustment of the orthodontic brace is not required. Because of the superelastic springs, the orthodontic brace will establish the desired spring force, even with a rather coarse tensioning.

Except for the above-mentioned advantages, an orthodontic brace according to the invention will be advantageous by having a very small thickness. Thus, it will not be uncomfortable for a user as the mounting bars may be moulded in a thin plastic material, which will not feel uncomfortable against the gums of the user. Moreover, this means that the orthodontic brace will be very sanitary in use. Furthermore, the orthodontic brace will be comfortable for the user because of a substantially constant force at a level, which does not cause unpleasantness due to high levels of force.

DESCRIPTION OF THE DRAWINGS

The invention will now be explained in further detail with reference to the accompanying drawings wherein FIGS. 16–18 show views of teeth for explaining the segmented orthodontic technique.

DETAILED DESCRIPTION OF THE PREFERRED EMBODIMENTS

Figure 1:
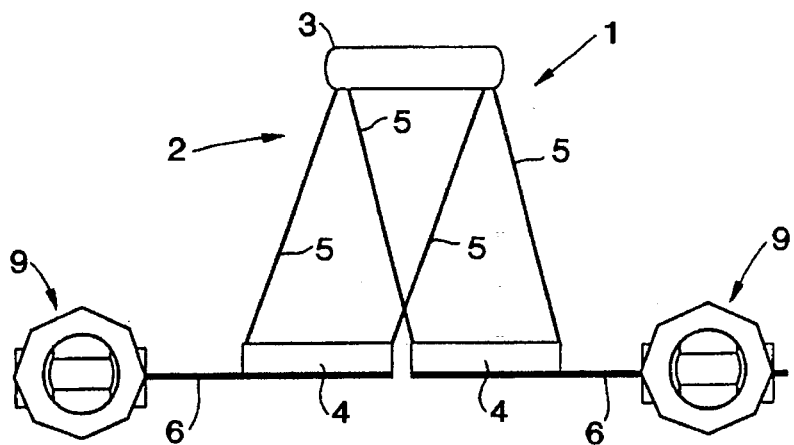
FIG. 1 shows a side view of an embodiment of an orthodontic brace according to the invention.

FIG. 1 shows an orthodontic brace 1 according to the present invention. The orthodontic brace comprises a guiding mechanism 2 with a bending stable upper mounting bar 3 and two bending stable lower mounting bars 4. The lower mounting bars 4 extend substantially parallel to the upper mounting bar. However, one or both of the lower mounting bars may be positioned at an angle compared to the upper mounting bar, as it will be explained later.

The upper mounting bar 3 is connected with each of the lower mounting bars by means of two substantially perpendicular and parallel wires 5. Each of the lower mounting bars 4 is connected with a rod 6. The rod 6 is intended for connection with an arch wire 7 (see FIG. 16) or directly with a bracket B (see FIG. 16) by means of fastening means 9, which will be further explained with reference to FIGS. 2–4.

The orthodontic brace comprises spring means of a superelastic material. In this embodiment the spring means are made up of the actual wires 5, which each is restrained in the mounting bars 3,4. The upper mounting bar is preferably made from a biologically compatible plastic material into which the wires 5 are moulded in order to establish the restraint. The lower mounting bars 4 may also be made from a plastic material into which the wire is moulded. Alternatively, the lower mounting bars 4 may be made from hollow tubes, which are brazed to the rods 6. Hereby, the ends of the wires 5 are fastened in the hollow tubes by a clamping of this, such that the superelastic material may be fastened without use of welding or brazing.

Each of the pair of wires 5 which connect to a lower mounting bar 4 is preferably formed by a single piece of wire having a circular section which is bent to a rectangular shape, the free ends of which are inserted into each end of the tube 30 (see FIG. 7), which constitutes a portion of the lower mounting bar 4. Thus, a side length of bent wire will be moulded into the upper mounting bar 3, while another side length will be clamped in a lower mounting bar 4. Hereby, a safe fastening is obtained so that each of the wires 5 acts as a restrained beam in the mounting bars 3,4.

Figure 2:
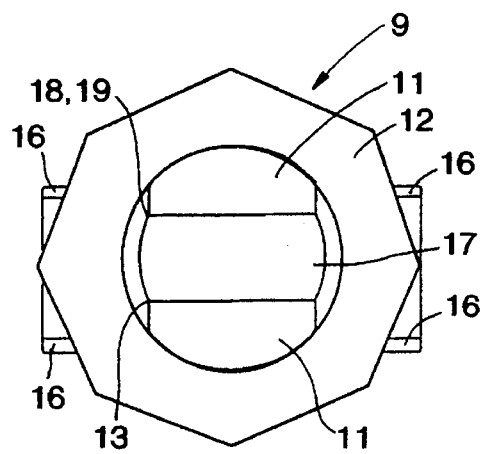
FIGS. 2–4 show views of fastening means, which forms part of the orthodontic brace shown in FIG. 1.
Figure 3:
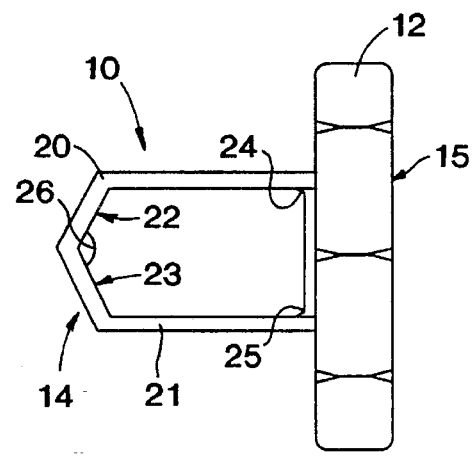
Figure 4:
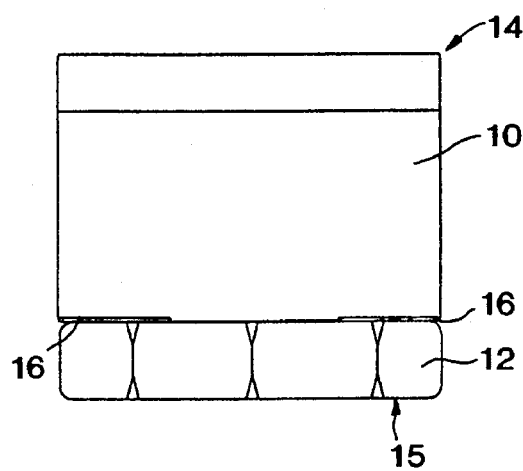

FIGS. 2–4 show fastening means 9 seen from different views. The fastening means 9 is made up of a U-shaped strip of sheet metal 10. At both corners in each end a rectangular portion of the sheet metal strip is removed so that a central portion remains, of which the outermost portion is bent to form a flap 11. In the shown embodiment the flap, which may pass through the interior of a nut 12, will be accommodated in a recess 13 which is formed in the side of the nut, which faces away from the lower portion 14 of the U. Hereby, the nut appears with an outer smooth side 15 as it is shown in FIGS. 3 and 4. Thus, the nut is held in place between the flap 11 and the top side 16 of the strip-shaped portion, which remains after the removal of a rectangular corner portion. Between the central flap-shaped portions 11 a displaceable pawl 17 is positioned, which is provided with a screw thread 18 that engages the screw thread 19 of the nut. Thereby, during the rotation of the nut 12 it will be possible to displace the pawl 17 in the space between the two branches 20,21 of the U. Hereby, a rod 6 and an arch wire 7 may be clamped in the interior of the U.

As the bottom 14 of the U is formed by two substantially plane surfaces 22,23, which form a V-shape, the wires 7 with varying diameters will be safely clamped. By providing the interior end of the pawl 17 having angled surfaces 24,25 the same effect is obtained. If the rods 6 have a rectangular cross section, the angled surfaces 24,25 of the pawl will have a very short extension, as illustrated in FIG. 3. If the rod 6 has a round cross section, the bottom side of the pawl will substantially correspond to the bottom of the U. The mutual angle 26 between the plane surfaces 22,23 may be between 30' and 120'. In order to obtain a torsion-stable fastening of wires 7 and rods 6, the strip has a width that is 2–10 times the distance between the branches 20,21 of the U.

Figure 5:
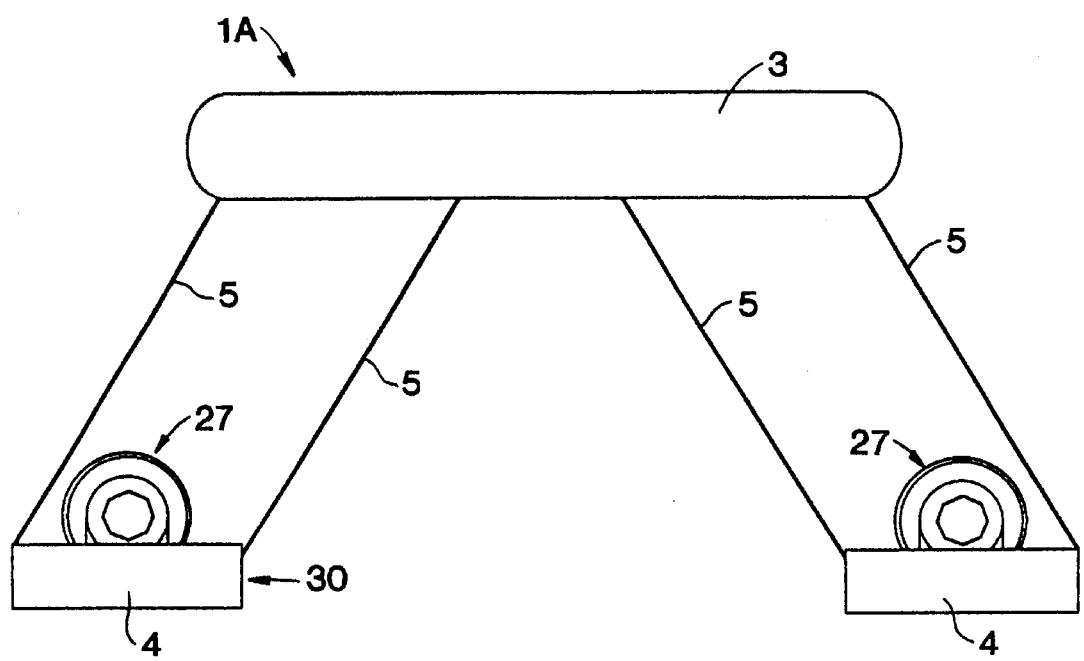
FIG. 5 shows a side view of another embodiment of an orthodontic brace according to the invention.

FIG. 5 shows another embodiment of an orthodontic brace 1A according to the invention. The orthodontic brace 1A substantially corresponds to the one shown in FIG. 1. In FIG. 5 the upper mounting bar 3 is made with a greater length so that each of the pair of wires 5,5 is positioned side-by-side and not overlaying each other. In this embodiment the lower mounting bars 4 are directly connected with fastening means 27.

Figure 6:
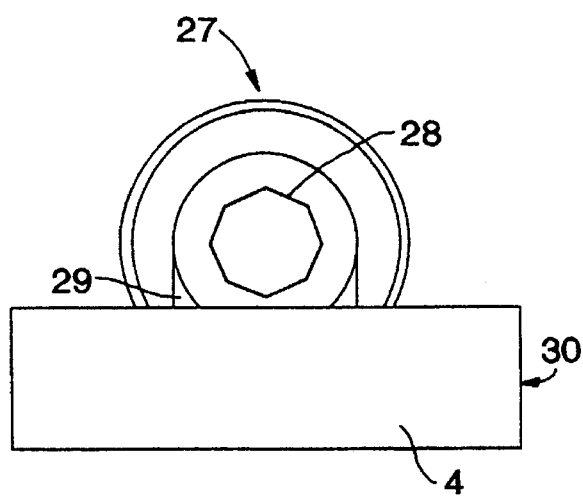
FIGS. 6 and 7 show views for illustrating fastening means, which is used in the orthodontic brace shown in FIG. 5, FIGS. 8–15 show views of further embodiments of orthodontic braces according to the invention.
Figure 7:
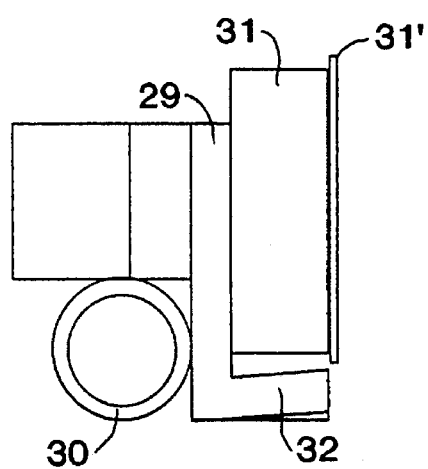

As it clearly appears from FIGS. 6 and 7, the fastening means basically function as the above-mentioned fastening means 9. The fastening means 27 comprise a so-called Allen screw 28. The screw 28 is mounted on a console 29 to which a tube 30 is also mounted. The tube 30 is used for accommodating the superelastic wire 5, which remains secured in this by pinching the tube 30. The arch wire or a wire length which is fastened directly onto the brackets on the teeth is clamped by an eccentric rotatable pawl 31 that is provided with a flange 31', which clamps the arch wire (not shown) in a spacing between the rotatable pawl 31 and a branch 32 which is connected with the console 29.

FIGS. 8–11 illustrate further embodiments of orthodontic braces according to the invention. It is noted that all embodiments are illustrated with fastening means of the integral type, which are illustrated in FIG. 5. However, it will also be possible to make these embodiments with separate fastening means, as illustrated in FIG. 1.

Figure 8:
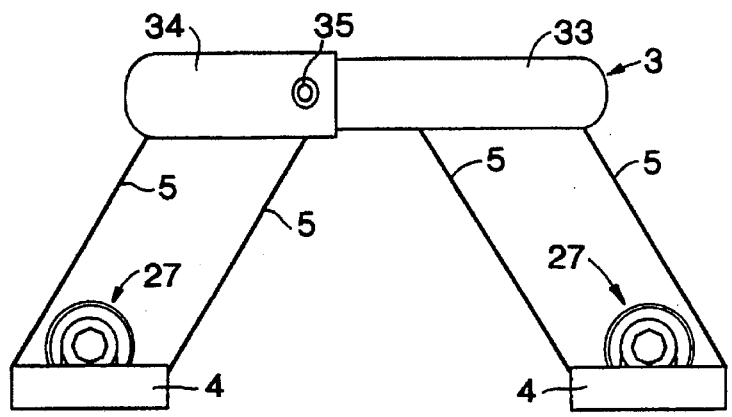

In FIG. 8 the upper mounting bar 3 is made with a length corresponding to the length shown in FIG. 5. The upper mounting bar consists of two mutual telescopic portions 33 and 34. The bar portion 33 has a smaller dimension so that the telescopic portion may be inserted in an outer bar portion 34. The mutual position of the two bar portions 33,34 is ensured by means of locking means 35, which may be a screw, a friction coupling, or similar releasable elements, which in active position may prevent a mutual displacing of the bar portions 33,34. Thus, this embodiment will be suitable for carrying out tooth movement over rather large distances, as the upper mounting bar is adjusted to a new length after an initial tooth movement.

Figure 9:
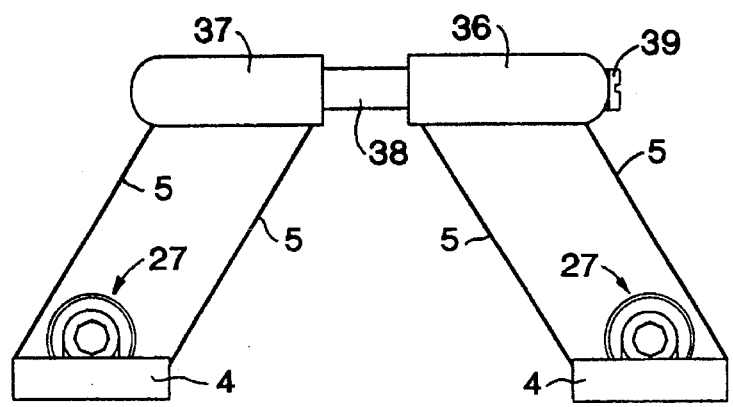

FIG. 9 illustrates another embodiment which substantially corresponds to the embodiment shown in FIG. 8. In FIG. 9 the upper mounting bar 3 consists of two end portions 36,37, which are mutually displaceable on a central rod 38. The mutual displacing of the bar portions 36,37 is established by means of a screw 39.

Figure 10:
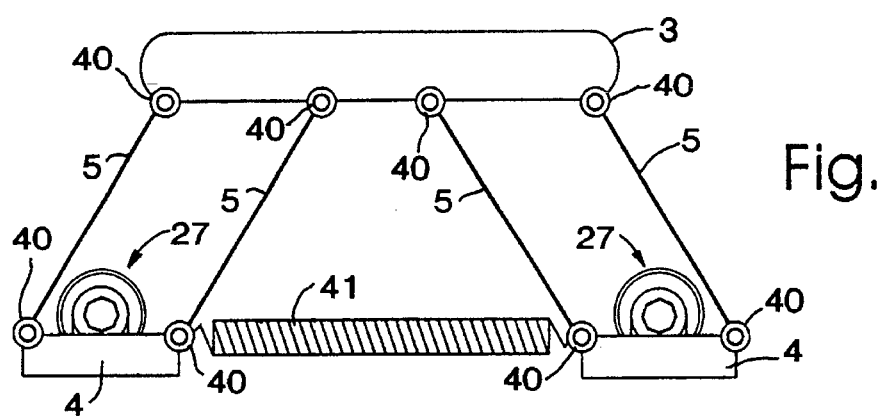
Figure 11:
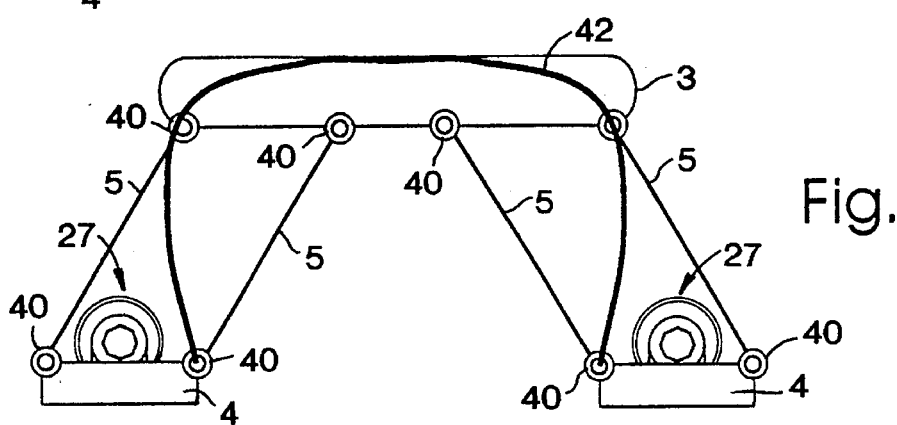

It is a common feature for the above-mentioned embodiments which are illustrated in FIGS. 1,5,8, and 9 that the the superelastic spring means are made up of restrained wires 5. In the two embodiments illustrated in FIGS. 10 and 11, the wires 5 are hinged to the upper 3 and lower 4 mounting bars via hinge connections 40. Thus, no springing may be obtained in the wires 5, which may be made from any suitable material. In FIG. 10 the spring force is established by means of a coil spring 41 of a superelastic material. The coil spring 41 is positioned between the two mounting bars 4, and may be both a tension and pressure spring. In FIG. 11 the spring is formed by a U-shaped spring 42, which is connected with the two mounting bars 4. The spring 42 may also be a tension or pressure spring.

As it appears from the above, all embodiments are able to carry out a correction of misaligned teeth both by joining and separating the teeth or tooth segments, which increases the flexibility of the orthodontic brace 1. Thus, an orthodontic brace according to the invention and to any embodiment illustrated in FIGS. 1–9 is completely symmetrical, and with equal effect will be able to be used for joining or separating teeth and/or tooth segments. FIGS. 12–15 illustrate embodiments of an orthodontic brace which is not symmetrical, and which makes more complicated orthodontic corrections possible.

FIGS. 12–15 illustrate two examples of orthodontic braces in which the guiding mechanisms 2 are asymmetrical by using wires 5 with different lengths. It is noted that the embodiment, which is illustrated in FIGS. 12 and 13, is made from elements which are identical with the elements in the embodiment which is shown in FIGS. 14 and 15.

FIGS. 12 and 13 illustrate a situation in which a wire 5' is shorter than the other wires 5, which is used to connect the upper mounting bars 3 with the lower mounting bars 4. The shorter wire 5' is connected with a projecting portion 43 of the upper mounting bar 3. In FIGS. 12 and 13 it is assumed that the left mounting bar 4 is fastened to the teeth which are secured, and which appear as an anchor, while the right mounting bar is connected with the tooth or the tooth segment to be moved (see succeeding FIGS. 24 and 25). FIG. 12 illustrates the orthodontic brace during the mounting on the teeth, and FIG. 13 illustrates the orthodontic brace after the tooth movement has taken place. In the embodiment shown in FIGS. 12 and 13, the lower mounting bar 4 illustrated in the right side is pivoted at the same time it is translated. This results in the connected bracket and the tooth being pivoted and translated.

In FIGS. 14 and 15 it is also the lower mounting bar 4 at the left side, which is intended to be positioned onto the secured teeth, while the mounting bar 4 at the right side is connected with the tooth or the tooth segment desired to be moved. In this situation a combined translation and rotation is also obtained, but the rotation will occur with opposite orientation of the rotation established in FIGS. 12 and 13.

In FIGS. 12–15 the orthodontic brace is shown with separate fastening means 9 of the type which are illustrated in FIGS. 2–4. However, it is also possible to provide these embodiments with fastening means 27 of the type which are illustrated in FIGS. 6 and 7.

In FIGS. 12–15 only one of the wires 5' has a shorter length than the others. However, it will also be possible that one of the wires 5 which are connected with the left mounting bar is made shorter and connected to the projecting portion 43 of the upper mounting bar 3.

Now that different embodiments of an orthodontic brace according to the invention have been explained, an explanation of how these orthodontic braces are used during the correction of irregular teeth will subsequently be given.

The use of the orthodontic brace according to the invention will be explained in connection with segmented orthodontic correction, as an understanding of the use in connection with the the straight-wire-technique will appear for a skilled in the art in the light of this explanation, which is given on the orthodontic brace and its use in connection with segmented orthodontic correction techniques.

FIG. 16 shows two tooth segments 44,45. The teeth in each tooth segment 44,45 are connected by means of an arch wire 7 and brackets 8. An orthodontic brace according to the invention is intended to be mounted on top of the arch wire 7 at a position 46 between the two teeth, as will be explained later.

The roots of the teeth 47 are positioned in the jaw bone, while the crowns 48 of the teeth are free. The brackets 8 used are adhered on the crowns 48 of the teeth. An actuation force of the teeth may only occur through the adhered brackets. The adhered brackets are arranged at a distance from the so-called centre of resistance 49 (see FIG. 17), which is in or at the root 47 of a tooth. The centre of resistance 49 is a well-defined feature within the orthodontic correction technique and is defined as the geometrical point where a force 50 on a segment is to be applied in order to provide a translational movement 51 for a tooth or a tooth segment in the direction of the force.

Figure 17:
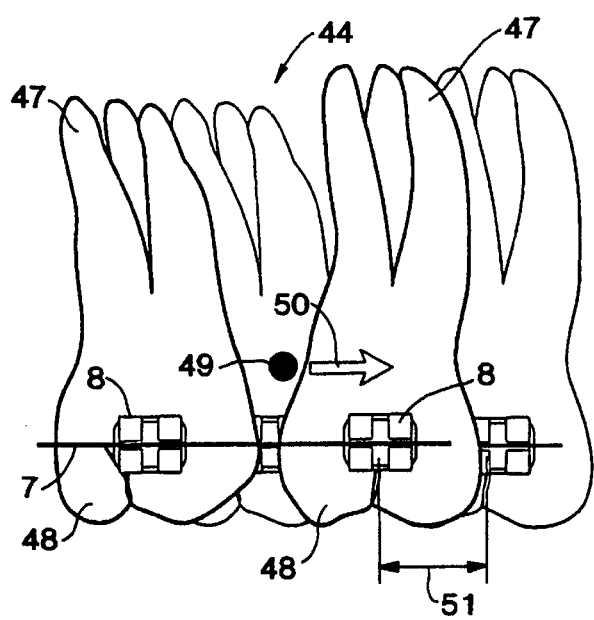

FIG. 17 shows the centre of resistance 49 of the segment 44. The position of the tooth segment 44 before the actuation force is shown with dark lines, while the position of the tooth segment 44 after a translational displacement is shown with light lines.

Figure 18:
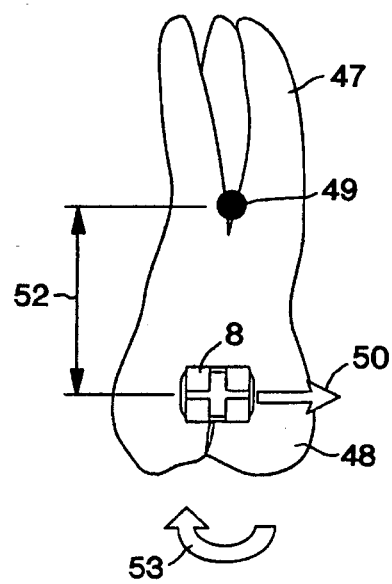

As a bracket 8 usually is positioned at a distance 52 from the centre of resistance 49, a moment 53 will be required as illustrated in FIG. 18, which together with the force 50 on a bracket, make it possible to obtain a translation of a tooth segment or a tooth. As mentioned previously, the relation between moment and force is of great importance in orthodontic correction of misaligned teeth. It is also commonly known that in order to obtain correct tooth movement, it is essential that during the tooth movement a force is added as constant as possible. This substantially constant force is obtained by using springs of a superelastic material.

Figure 19:
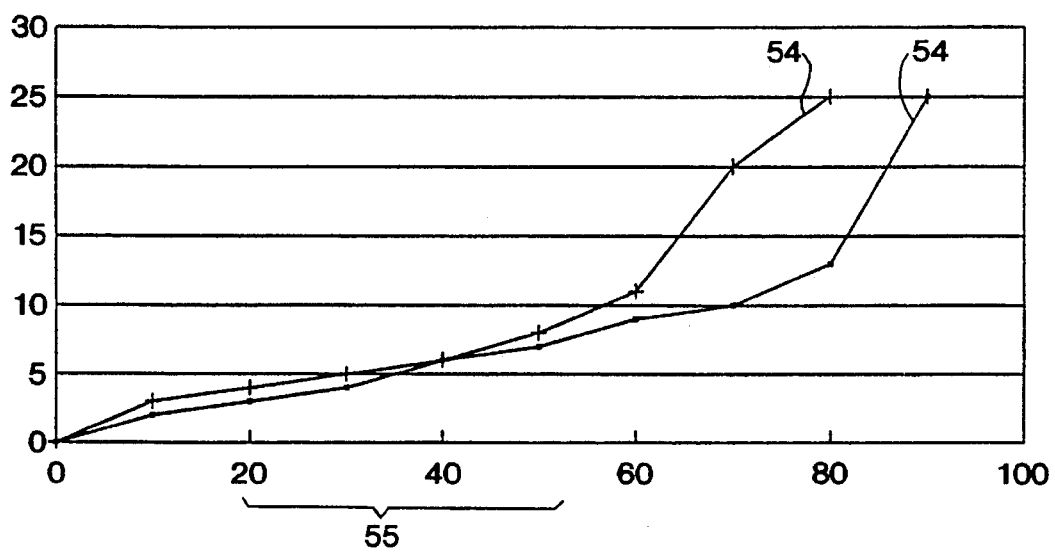
FIG. 19 shows a curve for illustrating the relation between rotation and moment of a wire-pair for supporting a lower mounting bar.
Figure 20:
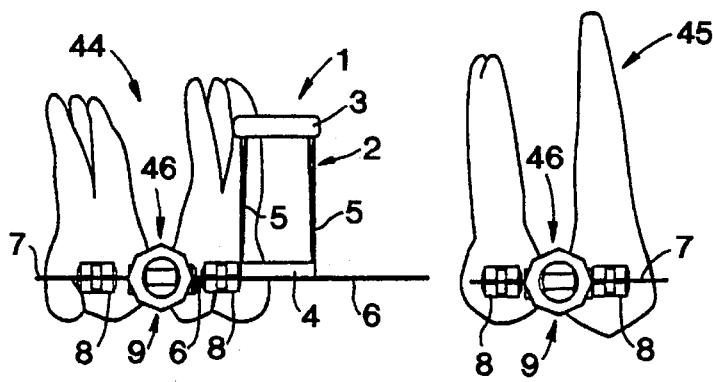
FIGS. 20–23 show views for illustrating the use of the orthodontic brace of FIG. 1 on the tooth segments shown in FIG. 16, FIGS. 24 and 25 show views for illustrating the use of the orthodontic brace of FIGS. 12 and 13, and FIGS. 26 and 27 show views corresponding to FIGS. 24 and 25 for illustrating the use of the orthodontic brace of FIGS. 14 and 15.

FIG. 19 shows a curve 54 for illustrating the relation between the bending moment measured in Ncm as abscissa and an angular motion measured in degrees as the ordinate for a restrained wire 5 for use by connecting a lower mounting bar 4 to an upper mounting bar 3. From this it appears that a very flat curve is obtained, so that even with a rather large rotation of the restrained wire 5, a substantially constant moment is obtained, and thereby a substantially constant force in a lower mounting bar 4. The substantially flat portion 55 of the curve is the area which is used in an orthodontic brace according to the invention. The orthodontic brace will always be dimensioned in such a way that the upper mounting bar 3 and each of the lower mounting bars 4 always have such a stiffness that they will not be subjected to any deformation of any importance by application of the spring forces which are established by using the brace. The fastening means 9,27 is also dimensioned in such a way that it does not bend during application of the forces to be transmitted.

FIGS. 20–23 show the use of the orthodontic brace 1 which is illustrated in FIG. 1 in connection with correction of the tooth segments 44,45, which are illustrated in FIG. 16. Initially the fastening means are positioned at positions 46 as the arch wire 7 is positioned between the branches of the U. Then the guiding system 2 is inserted with the individual portions in a neutral position, that is to say without being activated. The rod 6 at the left side is fastened with the fastening means 9. Next the brace 1 is activated (FIG. 21), and the rod at the right side is fastened with the fastening means 9 at the right side. The orthodontic brace 1 is now in an active state secured between the two tooth segments 44,45. In the shown situation the tooth segment 45 has to be displaced translationally against the tooth segment 44.

Figure 21:
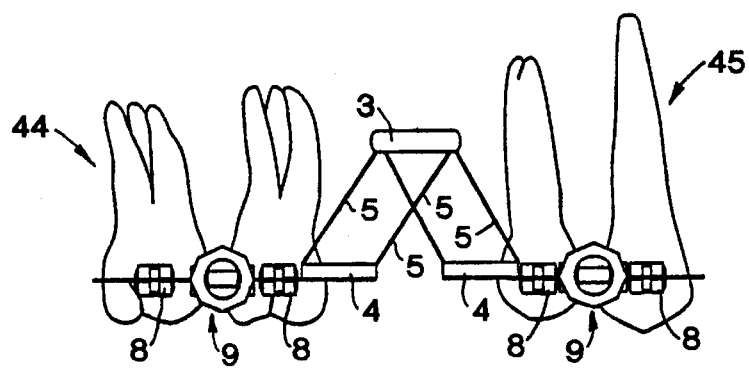
Figure 22:
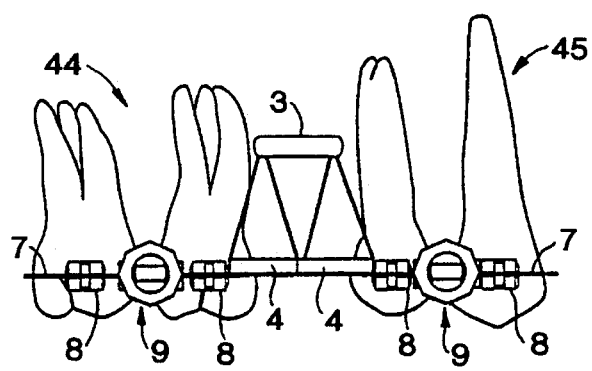
Figure 23:
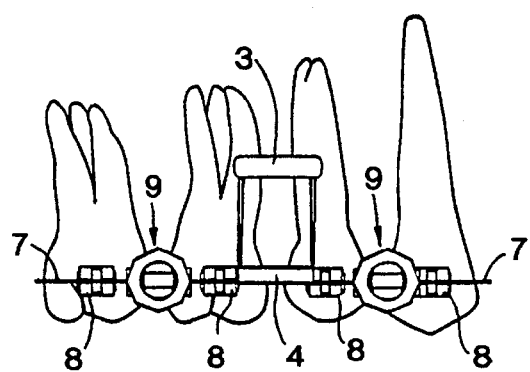

The actual mounting and the activating of the orthodontic brace is rather uncomplicated as the joining force used will substantially be constant even with a rather large deflection of the restrained wires 5. In FIG. 22 the tooth segment 45 is partially guided towards the tooth segment 44, and in FIG. 23 the two tooth segments 44,45 are brought completely together, and the correction of the misaligned teeth is finished. Thus, it will be possible to execute the steps of orthodontics, which are illustrated in FIGS. 21–23, by a single activating of the orthodontic brace 1.

If a very great distance appears between the tooth segments 44,45, an extra activating may be necessary. Alternatively, a very great distance between the tooth segments 44,45 will necessitate use of an orthodontic brace of the type which is shown in FIGS. 5,8, or 9.

Figure 24:
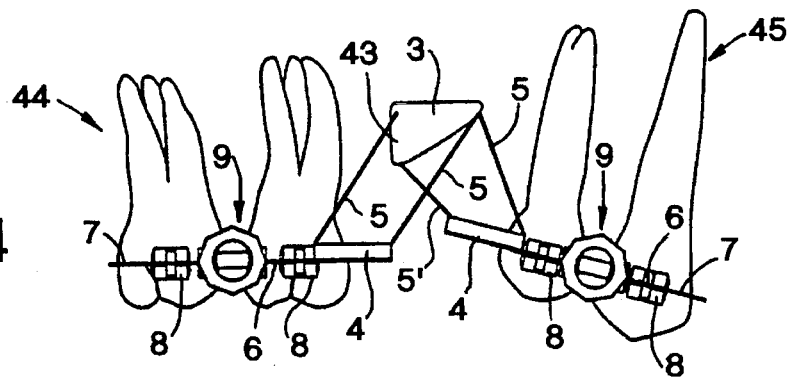
Figure 25:
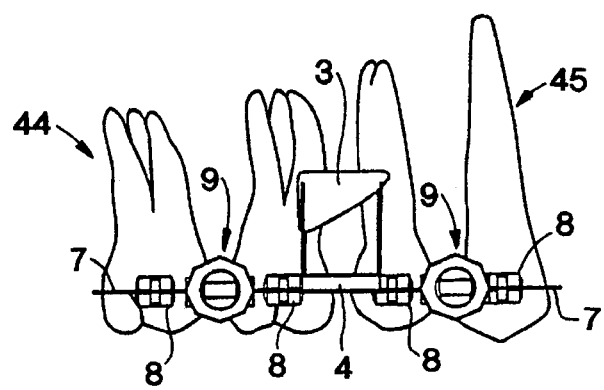

FIGS. 24 and 25 show the use of the orthodontic brace 1 which is shown in FIGS. 12 and 13. The orthodontic brace is mounted between the tooth segments 44 and 45. In this situation not only a translation should be induced on the tooth segment 45 as it was illustrated in FIGS. 20–23. The tooth segment 45 has to provide a translation and a counter clockwise rotation. By using an orthodontic brace with a shorter wire 5' positioned at the side, which faces the secured segment, the lower connecting bar 4 at the right side, and accordingly the tooth segment will be displaced and rotated at the same time. After joining the tooth segments 44 and 45, the orthodontic brace will hold it in the shown position in FIG. 25. Thus, the brace 1 has been able to carry out a combined translation and rotation by a single mounting and a single activating.

Figure 26:
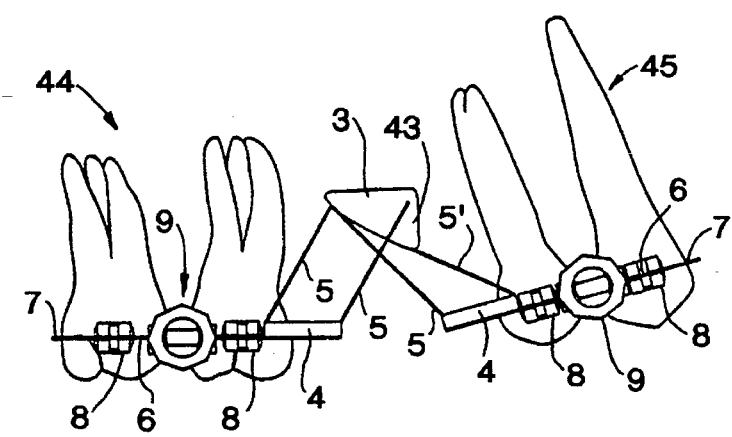
Figure 27:
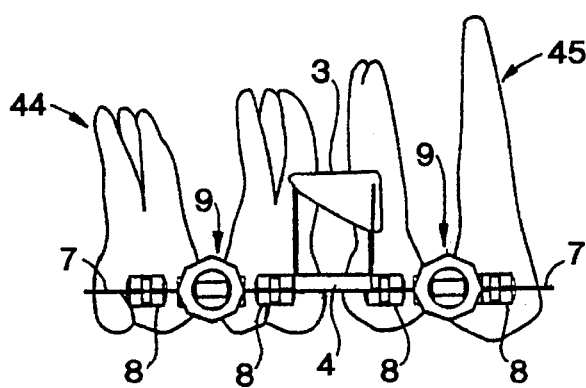

FIGS. 26 and 27 illustrate a correction of irregular teeth which is analogous to the correction shown in FIGS. 24 and 25. In this use the shorter wire 5' is positioned nearest the tooth segment 45 which is to be displaced and rotated. Consequently, this tooth segment is provided with a counter clockwise rotation simultaneously with the translation in the direction towards the tooth segment 44.

FIGS. 24–27 illustrate two specific situations of orthodontic correction. However, all possible relative movements between the segments 44,45 may be obtained by changing the points of restraint, and thereby the lengths of the wires 5 used.

By using an orthodontic brace 1 according to the invention, a displacing of a tooth or a tooth segment 45 will occur on the basis of the concrete form of the guiding mechanism 2 consisting of the upper mounting bar 3, the lower mounting bars 4, and the wires 5 positioned between them. As the guiding mechanism 2 is effected by the spring force, which is formed by superelastic spring material 5,41,42, a substantially constant force is obtained which may be kept at a rather low level that is optimized regarding the biomechanical system.

Because of bending stability in the mounting bars 3,4 and in the fastening means 9,27, and possible attached rods and arch wires 6,7, the movement of the element of the guiding mechanism 2 will give rise to a self-adjusting contribution of moment which is exerted on a tooth or a tooth segment via the adhered brackets 8. If the spring forces are exerted to a bracket 8 at a distance from the centre of resistance so that a moment is formed, the torsion stable engaging of the arch wire with a bracket 8 will give rise to a compensating moment 53. Thus, the use of an orthodontic brace 1 according to the invention will be very simple, as a user does not need to carry out individual adjustments in order to adjust an established spring force and an established moment to a given situation of orthodontic correction.

When the user has established whether there is a need for a pure translation or a translation combined with a rotation, an orthodontic brace is chosen which is mounted and activated, after which a correct force and a possible contribution of moment is exerted automatically because of the form of the guiding mechanism 2. The orthodontic brace 1 is very easy to use as it merely requires fastening of a nut 12 or a screw 28. The actual fastening may take place by means of a per se known torque wrench to ensure a correct fastening.

We claim:

1. An orthodontic brace for moving teeth comprising force-transmitting means connected with the teeth to be moved for transmitting an actuation force to the teeth; a guiding mechanism with a bending stable, upper mounting bar, two bending stable, lower mounting bars which extend substantially parallel to the upper mounting bar, and a spring means of a superelastic material; and a fastening means for connecting the guiding mechanism with the force-transmitting means, said spring means resiliently actuating said two lower mounting bars and causing desired movement of said teeth.

2. An orthodontic brace according to claim 1, wherein said spring means comprise two pairs of wires made of superelastic material, each pair of wires comprising two parallel wires which connect said bending stable upper mounting bar with a respective bending stable lower mounting bar.

3. An orthodontic brace according to claim 2, wherein the superelastic wires are restrained in the mounting bars by moulding into the upper mounting bars and by clamping into a tube, which together with a bar, which is used for fastening the orthodontic brace, constitutes each of the lower mounting bars, said tubes being fastened to the bar by soldering or welding.

4. An orthodontic brace according to claim 1, wherein said guiding mechanism includes wires connected with the mounting bars by a huge joint, and wherein said spring means comprises a U-shaped spring or a coil spring mounted between the two lower mounting bars.

5. An orthodontic brace according to claim 2, wherein at least one of the wires has a length shorter than the length of the other wires as they are mounted in a projecting portion of a mounting bar.

6. An orthodontic brace according to claim 1, wherein the upper mounting bar is made of two telescopic portions, and the lower mounting bars are connected with each of said telescopic portions.

7. An orthodontic brace according to claim 1, wherein the fastening means are constituted of a U-shaped clamping device which is intended for accommodating a rod-shaped portion of the lower mounting bar and an arch wire, wherein the U-shaped clamping device is formed by a U-shaped strip in which the four rectangular corner portions are removed in such a way that central portion of the outermost portions of the U-shaped strip may accommodate a nut, which is secured in a position for rotation as outermost central portions of a branch of the U-shaped strip is bent outwardly for formation of flaps which prevent removal of the nut as a displaceable pawl is provided between the two branches of the U-shaped strip, said pawl being in engagement with the nut through a thread.

8. An orthodontic brace according to claim 7, wherein a distance between the branches of the U-shaped strip substantially correspond to the cross dimension of the tubular rod of the mounting bar and the cross dimension of the arch wire, and the width of the U-shaped strip is between 2 and 10 times said distance between the branches.

9. An orthodontic brace according to claim 7, wherein the flaps formed on the outermost central portions of the branches of the U-shaped strip have such a dimension that the central end portion of the U-shaped strip in a compressed state may pass through the nut.

10. An orthodontic brace according to claim 7, wherein both a bottom of the U-shaped strip and the end of the displaceable pawl facing an interior of the U-shaped strip are made of two substantially plane surfaces which form a V-shape having a mutual angle of between 30° and 120°.

* * * * *